United States Patent [19]

Yokogawa et al.

[11] Patent Number: 4,522,688
[45] Date of Patent: Jun. 11, 1985

[54] PROCESS FOR RECOVERY OF CYCLOPENTADIENES

[75] Inventors: Akira Yokogawa, Kasukabe; Asao Takahashi, Omiya; Isao Maruyama, Chihara; Takao Hosaka, Chiba, all of Japan

[73] Assignee: Maruzen Petrochemical Co., Ltd., Tokyo, Japan

[21] Appl. No.: 545,661

[22] Filed: Oct. 26, 1983

[30] Foreign Application Priority Data

Oct. 29, 1982 [JP] Japan .................. 57-190968

[51] Int. Cl.³ .............................. B01D 3/14
[52] U.S. Cl. ...................... 203/28; 203/78; 203/80; 203/84; 585/354; 585/803; 585/832
[58] Field of Search .............. 203/28, 78, 80, 84; 585/805, 806, 803, 809, 832, 354, 810

[56] References Cited

U.S. PATENT DOCUMENTS 2,439,307 4/1948 Legatski .................. 585/832
2,636,056 4/1953 Jones ...................... 585/832
2,733,279 1/1956 Wilson et al. .
2,733,280 1/1956 Hamner .
2,813,134 11/1953 Johnson .................. 585/354

FOREIGN PATENT DOCUMENTS 239513 7/1962 Australia .................. 585/832
64622 4/1982 Japan .

Primary Examiner—William F. Smith
Attorney, Agent, or Firm—Frishauf, Holtz, Goodman and Woodward

[57] ABSTRACT

The process gives highly pure cyclopentadiene and methylcyclopentadiene from a cracked gasoline fraction. The merit of the process is that cyclopentadiene and methylcyclopentadiene are recovered by adding a simple distillation system to a conventional cracked gasoline treating plant without altering the plant and operating conditions thereof. An internal reflux stream is withdrawn from the stripping section of a BTX column of a conventional cracked gasoline treating plant, and is sent to a depolymerization-distillation column operated at a bottom temperature of 160°–230° C. The overhead stream of the column is sent to a cyclopentadiene column operated at a bottom temperature of 160°–230° C. Cyclopentadiene is recovered from the overhead of the column, and the bottom stream is sent to methylcyclopentadiene column operated at a bottom temperature of 170°–210° C. Methylcyclopentadiene is recovered from the overhead of the column.

6 Claims, 2 Drawing Figures

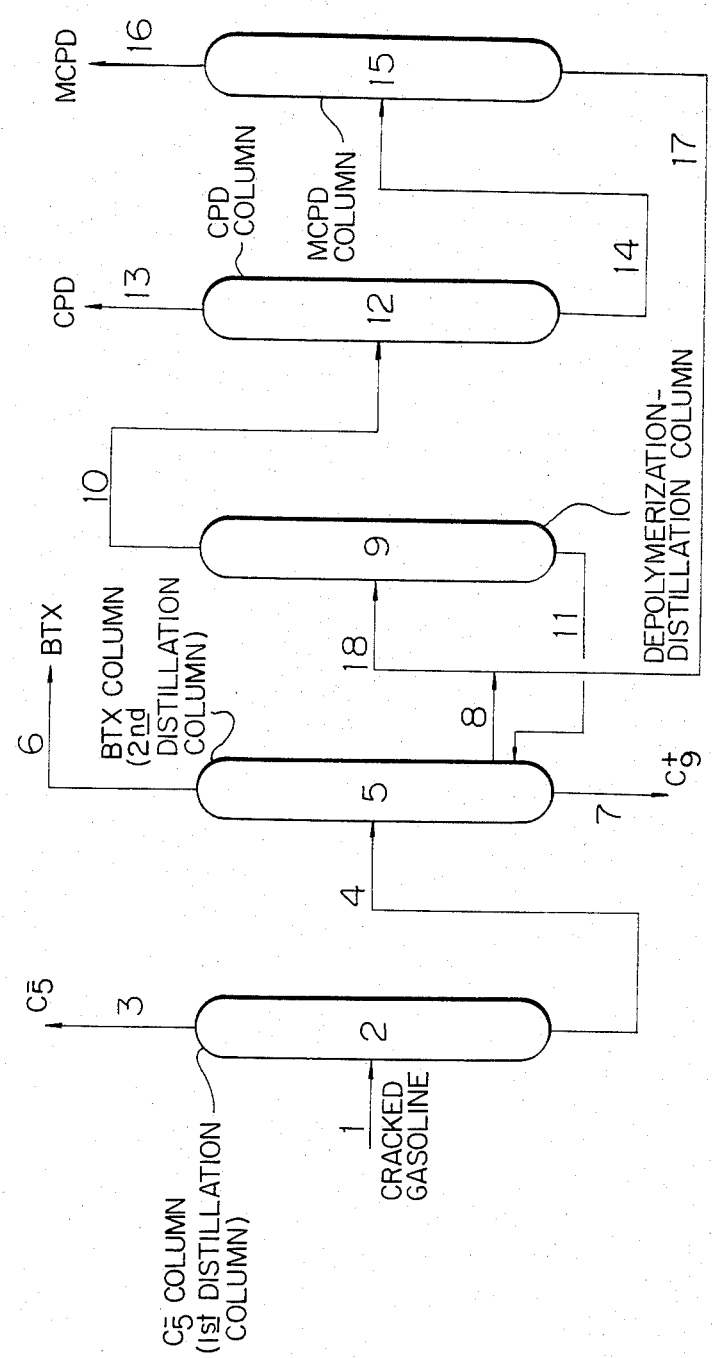

PROCESS FOR RECOVERY OF CYCLOPENTADIENES

BACKGROUND OF THE INVENTION

1. Field of the Invention

The present invention relates to a process for separation and recovery of cyclopentadiene (hereinafter called CPD), or CPD and methylcyclopentadiene (hereinafter called MCPD) in high purity from cracked gasoline fraction, which is produced as a by-product of ethylene production by thermal or steam cracking of a petroleum fraction such as naphtha, kerosene, and gas oil.

The process of the present invention is advantageous because it allows an economical separation of highly pure CPD, or highly pure CPD and MCPD merely by addition of simple processing units, without any alteration of the process and operating conditions of the conventional process for treatment of cracked gasoline, and also because it reduces the load on the hydrogenation reactor in the benzene-toluene-xylene (hereinafter called BTX) recovery process. The reduction of the load on the hydrogenation reactor not only allows saving of hydrogen consumption in the reactor, but also prolongs the catalyst life.

CPD is a useful material, for example, as a raw material of Diels-Alder reactions, and MCPD also is a useful material. For example, MCPD is used as a hardener of epoxy resins. At present, the production of MCPD is low and MCPD is an expensive material.

2. Description of the Prior Art

In the production of ethylene by thermal or steam cracking of a petroleum fraction such as naphtha, kerosene, and gas oil, the cracked gasoline fraction which is formed as a by-product, is usually processed by two distillation columns in order to recover BTX from the fraction, and the BTX fraction is then passed to an aromatics extraction unit, in which highly pure BTX are recovered.

The cracked gasoline fraction also contains about 3-7% of CPD and about 1-2% of MCPD. However, treatment of CPD is not easy because it is thermally unstable and readily undergoes dimerization and codimerization. Also, the separation of MCPD from cracked gasoline by distillation is not easy because of its low concentration and because its boiling point (73° C.) is close to the boiling point of benzene (80° C.), which is present in large amount in cracked gasoline.

Moreover, the separation and recovery of MCPD is difficult because it is unstable and readily dimerizes or codimerizes with other compounds.

With regards to processes for separation and recovery of CPD and MCPD from cracked gasoline fraction, U.S. Pat. No. 2,733,279 proposes a process which comprises obtaining a $C_5$-$C_7$ fraction by distillation of a cracked gasoline fraction, removing light fractions by heating the fraction, and recovering CPD and MCPD by depolymerization-distillation of the dimers. U.S. Pat. No. 2,733,280 proposes a process which comprises recovering a fraction containing the dimers by distillation under reduced pressure, followed by recovering CPD and MCPD by depolymerization-distillation of the dimers.

However, the contents of CPD and MCPD in cracked gasoline are only in the range of about 3-7% and 1-2%, respectively, and because of their low contents, a large amount of cracked gasoline should be processed, which requires a large apparatus for this process, and a large amount of energy is required for the distillation, dimerization, and depolymerization processes. Therefore, these processes are economically not advantageous.

SUMMARY OF THE INVENTION

In order to overcome these disadvantages, we have made an extensive study on thermal behavior of CPD and MCPD during processing of a cracked gasoline fraction which is formed as a by-product from an ethylene production plant, and found that, during the processing, CPD and MCPD dimerize rapidly at a temperature range of 80°-150° C., the dimer of CPD (b.p. ca. 170° C.) depolymerizes readily at 160°-230° C., and the dimer of MCPD (b.p. ca. 200° C.) depolymerizes readily at 170°-230° C. It was also found that the depolymerization temperature of the codimer of CPD and MCPD is nearly equall to that of the CPD dimer, and the depolymerization temperatures of interdimers of MCPD with isoprene, 1,3-pentadiene, styrene, methylstylene, etc. are higher than that of the MCPD dimer. On the basis of these findings, we have found a simple, energy-saving process for an efficient separation and recovery of highly pure CPD and MCPD by combining a simple recovery process into a conventional cracked gasoline treating process described above.

Therefore, the first object of the present invention is to provide a process which allows an easy recovery of CPD, or CPD and MCPD in high purity, which can be combined to the conventional plant for treatment of a cracked gasoline fraction, formed as a by-product of thermal or steam cracking of a petroleum fraction such as naphtha, kerosene, and gas oil, without alteration of the processing conditions of the cracked gasoline fraction.

The second object of this invention is to provide a process for recovery of highly pure CPD, or CPD and MCPD from a cracked gasoline fraction with small energy consumption and at the same time the process can minimize the load on the hydrogenation reactor of BTX recovery process.

Other object of this invention will be obvious and will appear hereinafter.

Thus, the gist of the present invention resides in a process for recovery of CPD from a cracked gasoline fraction which comprises withdrawing the internal reflux stream from the stripping section of a BTX distillation column, designed to recover benzene, toluene, and xylene as the overhead fraction from cracked gasoline fraction which is formed as a byproduct in the thermal or steam cracking of a liquid hydrocarbon, sending the internal reflux stream to a depolymerization-distillation column in which the stream is depolymerized by heating at 160°-230° C. for 10-200 minutes, returning the bottom stream of the depolymerization-distillation column to the BTX column at a position which is situated below the withdrawing position, sending the overhead stream to a CPD distillation column which is operated at a bottom temperature of 160°-230° C. with a residence time of 0.25-6 hours, and distilling out CPD from the overhead of the CPD column, and when simultaneous production of CPD and MCPD is desired, in the process described above, the depolymerization-distillation column is operated at the bottom temperature of 170°-230° C. and the bottom stream of CPD column is sent to MCPD column which is operated at a bottom temperature of 170°–210° C. with a residence time 0.5–5 hours, and MCPD is distilled out from the overhead of the MCPD column.

BRIEF DESCRIPTION OF THE DRAWINGS

The present invention is described in more detail below with reference to the attached Figures. For the sake of simplicity, several equipments such as pumps, heat exchangers, reflux drums, etc. which are not indispensable for the explanation are omitted, and only the parts which are essential for understanding of the present invention are shown in the Figures.

FIG. 2 shows a flow diagram of an example of the process of the present invention, in which the process of the present invention for recovery of CPD and MCPD is combined with the conventional process for treatment of cracked gasoline shown in FIG. 1. In FIG. 2, the same numbers are given for the parts which are common to the two Figures.

DETAILED DESCRIPTION OF THE INVENTION

Figure 1:
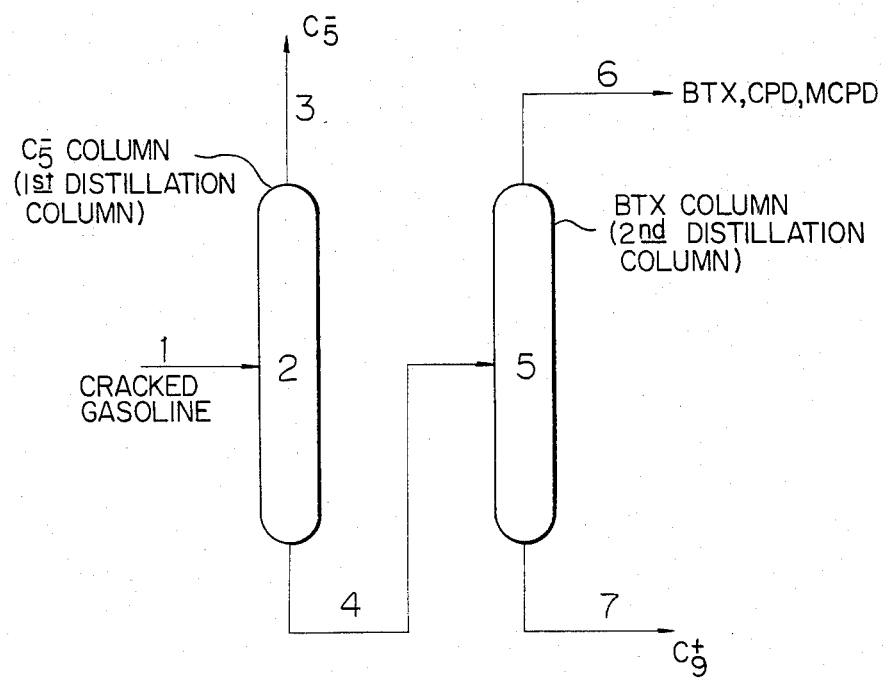
FIG. 1 shows the flow diagram of a usual process for treatment of cracked gasoline which is produced as a by-product from a conventional ethylene production plant.

Cracked gasoline which is produced as a byproduct of an ethylene production plant is charged to the first distillation column 2 ($C_5^-$ column) through line 1, and the $C_5^-$ fraction is withdrawn from the overhead, while the bottom fraction is passed to the second distillation column 5 (BTX column) through line 4. Within this column, the $C_9^+$ fraction is withdrawn from the bottom through line 7, while the BTX fraction is withdrawn from the overhead through line 6, passed to a hydrogenation reactor (not shown in the Figures), and then charged to an aromatics extraction unit (not shown in the Figures).

The CPD and MCPD in the cracked gasoline, which is charged to the first distillation column 2, exist in part as dimers or codimer of cyclopentadiene and methylcyclopentadiene (hereinafter simply called codimer), and about 10–30% of CPD and MCPD monomers are converted further to the dimers or the codimer in the first distillation column.

The CPD in the cracked gasoline which is charged to the second distillation column 5 exists solely as the dimer or the codimer, and the MCPD in the charge exists as the monomer, dimer, or codimer. The ratio of the monomer to the dimer or codimer varies with the operating conditions, but are generally in the range of 3:1–1:1.

In order to recover completely the BTX fraction, the second distillation column 5 is operated at a bottom temperature of about 200°–230° C. with a residence time of 1–2 hours. Under these operating conditions, the dimers and codimer of CPD and MCPD are almost completely depolymerized to CPD and MCPD, and depolymerized CPD and MCPD are withdrawn from the overhead with the BTX fraction and are passed to the hydrogenation reactor.

During this process, most of the CPD and MCPD in cracked gasoline are concentrated as monomers in the overhead fraction of the second distillation column 5. Therefore, in a superficial view, it appears reasonable to recover CPD and MCPD by distillation of This fraction. However, it is extremely difficult to recover highly pure MCPD by distillation of this fraction because this fraction contains a large amount of benzene, the boiling point of which is close to that of MCPD. Consequently, we have made study on a process for recovery of CPD and MCPD which comprises separating CPD and MCPD dimers and codimer without depolymerization of the dimers and codimer of CPD and MCPD from the BTX fraction, in the cracked gasoline charged to the second distillation column 5, followed by depolymerization-distillation thereof, and we have established the present invention.

All or a part of the internal reflux stream in the second distillation column 5 is withdrawn from a distillation plate which is as close as possible to the bottom, and is passed to the bottom of the depolymerization-distillation column 9 through line 8. It is in order to withdraw, at a high temperature, the fraction which is rich in dimers and codimer of CPD and MCPD without reducing the efficiency of stripping section of the second distillation column 5 that the internal reflux stream in the second distillation column 5 is withdrawn from a nozzle which is as close as possible to the column bottom. Because the temperature of the internal reflux stream at the withdrawing nozzle of the second distillation column 5 is about 170°–200° C. and the residence time of the internal reflux stream between the charge plate and the withdrawing plate is generally within ten minutes, the dimers and codimer of CPD and MCPD which are charged to the second distillation column 5 are passed to the depolymerization-distillation column 9 without any appreciable depolymerization.

The composition of dimers and codimer of CPD and MCPD in this stream varies with the composition of the raw material used for the ethylene production, cracking temperature, distillation conditions, etc., but, in general, CPD dimer is present in the range of 3–6 wt % and MCPD dimer and the codimer are present in the range of about 0.4–1.5 wt %.

When only CPD is to be recovered, CPD dimer is almost completely depolymerized to CPD monomer by operating the distillation in the depolymerization-distillation column 9 at a bottom temperature of 160°–230° C., preferably at 200°–230° C. with a residence time of the bottom of 10–200 minutes, and the CPD monomer is transferred from the overhead to a CPD column 12 through line 10. When CPD and MCPD are to be recovered, it is advisable to maintain the bottom temperature over 170° C. and preferably 200°–230° C. Heavy fractions rich in $C_9^+$ and xylene fractions are returned from the bottom of column 9 to the second distillation column 5 through line 11. It is desirable that the position of this returning should be one plate below the plate on which the withdrawing line 8 is attached.

It is preferable to take out a part of the xylene and $C_9^+$ fractions from the overhead of the depolymerization-distillation column 9 together with CPD and MCPD and pass it to the CPD distillation column 12. It is because the presence of CPD and MCPD in high concentration in the CPD column 12 tends to foul the distillation column due to their polymerization, while in the presence of $C_9^{30}$ and xylene fractions, they act as a kind of diluents and thus inhibit their polymerization. The amount of $C_9^+$ and xylene fraction which is charged to the CPD column 12 is preferably 20–200 weight parts per 100 weight parts of CPD and MCPD. It is advisable to operate the depolymerization-distillation column under an overhead pressure of 0–5 Kg/cm².G at a temperature of 140°–210° C.

When CPD and MCPD are to be recovered, CPD is withdrawn from the overhead by operating the distillation in the CPD column 12 at a bottom temperature of 160°-230° C., bottom residence time of 0.25-6 hours, overhead pressure of 0-2 Kg/cm$^2$.G, and an overhead temperature of 35°-80° C., while MCPD is converted to the dimer, and is withdrawn with the xylene and C$_9$+ fractions from the bottom, and is charged to an MCPD distillation column 15 through line 14. In this case, it is essential to keep the bottom temperature within the CPD column 12 above 160° C. It is because CPD and MCPD dimerize or codimerize quite readily in the CPD column, and when the temperature is kept below 160° C., the dimer and the codimer of CPD which are formed in the column are withdrawn with the dimer of MCPD and are passed to the MCPD column 15, and thus lower the purity of MCPD. By keeping the temperature above 160° C., the dimer of CPD and the codimer are almost completely depolymerized, thus they will not be transferred to the MCPD column 15.

It is not preferable to raise the distillation temperature above 230° C. because it causes the polymerization other than dimerization of CPD and MCPD, and thus results in a reduced yield and fouling of the distillation column. When only CPD is to be recovered, the bottom temperature may also be kept at 160°-230° C., and the bottom stream may be charged back to either the depolymerization-distillation column 9 or to the BTX column. The choice of the ways is determined by the operating conditions, and when the content of the dimer and codimer of CPD in the CPD column bottom stream is high, it is preferable to charge the said stream back to the depolymerization-distillation column.

By performing the distillation in the MCPD column 15 at a bottom temperature of 170°-210° C. with a residence time of the bottom of 0.5-5 hours, overhead pressure of 0-2 Kg/cm$^2$.G, and at an overhead temperature of 65°-115° C., MCPD dimer is depolymerized to MCPD, which is recovered from the overhead. It is preferable to circulate the undecomposed MCPD dimer and codimer, together with C$_9$+ and xylene fractions, back to the depolymerization-distillation column 9 through line 17.

It is not economical to operate the process at a bottom temperature of column 15 below 170° C. because MCPD dimer depolymerizes only insufficiently and results in an increase in the amount of MCPD dimer which circulates as the bottom stream of the MCPD column, while it is not preferable to operate above 210° C. because it lowers the purity of MCPD as a result of the depolymerization of interdimers of CPD and MCPD with styrene, methylstyrene, etc., which are present in the C$_9$+ fraction.

As described above, in accordance with the process of the present invention, in which a simple process for recovery of CPD an MCPD is combined to a process for recovery of BTX from cracked gasoline, highly pure CPD and MCPD can be recovered by a simple and energy-saving process without the need of a process for dimerization of CPD and MCPD, and the process of the present invention has an additional advantage in that it can remarkably reduce the load on the hydrogenation reactor because the present process greatly reduces the concentration of CPD and MCPD in the BTX fraction from the overhead of the second distillation column 5. It is apparent that a process for dimerization of CPD and MCPD may be combined to the present process described above, in order to recover a large amount of CPD and MCPD. In this case, however, the dimerization process should be inserted after the first distillation column 2. It is because a large amount of conjugated diolefins such as isoprene and 1,3-pentadiene are present in the fraction before the first distillation column 2, that CPD and MCPD interdimerize with such conjugated diolefins, and that the purity of MCPD is lowered by partial depolymerization of such interdimers in the MCPD distillation column 15.

In the practice of the process of the present invention, the distillation columns are not restricted to plate columns, and any columns such as packed columns may be used. Moreover, anti-oxidants, which are known in the art, may be added to the CPD column and the MCPD column, and other substances such as steam may be present as diluents.

DESCRIPTION OF THE PREFERRED EMBODIMENT

The present invention will be explained below with reference to an example. Example The internal reflux stream withdrawn from a distillation plate near the bottom of a distillation column 5 conventionally used for recovery of BTX from cracked gasoline, was used as the raw material. The operating conditions of the BTX column 5 are shown in Table 1, while the composition of the internal reflux stream withdrawn from BTX column is shown in Table 2.

TABLE 1

| Operating Conditions of the BTX Column | |
|---|---|
| Overhead pressure | 0.3 Kg/cm$^2$ · G |
| Bottom temperature | 200° C. |
| Overhead temperature | 113° C. |
| Number of distillation plates in the enriching section | 13 |
| Number of distillation plates in the stripping section | 12 |
| Internal reflux stream withdrawal | 22nd plate from the top |
| Temperature of the withdrawn stream | 175° C. |

TABLE 2

| Composition of the Internal Reflux Stream Withdrawn | |
|---|---|
| Component | wt % |
| CPD dimer | 3.4 |
| MCPD dimer (including codimer) | 0.6 |
| Xylenes | 7.0 |
| C$_9$+ | 89.0 |

The stream with the composition described above was charged at the rate of 6,000 g/hr to a bottom of a depolymerization-distillation column (an Oldershow distillation column with five plates, with the size of 35 mm diameter, 300 mm height and equipped with a heater at the bottom). The operating conditions of the depolymerization-distillation column are shown in Table 3.

TABLE 3

| Operating Conditions of the Depolymerization-Distillation Column | |
|---|---|
| Overhead pressure | 3 Kg/cm$^2$ · G |
| Overhead temperature | 193° C. |
| Column bottom temperature | 220° C. |

The composition of the overhead stream of depolymerization-distillation column is shown in Table 4.

TABLE 4
Composition of the Overhead Stream of the Depolymerization-Distillation Column

| Component | wt % |
| --- | --- |
| CPD | 51.2 |
| MCPD | 8.0 |
| Xylenes | 27.5 |
| C$_9$+ | 13.3 |

The overhead fraction which was withdrawn at a rate of 330 g/hr with the composition shown in Table 4 was charged to middle part of a CPD column (an Oldershow distillation column with 15 plates, with the size of 35 mm diameter, 800 mm height, and equipped with a heater at the bottom). The operating conditions of the CPD column are shown in Table 5.

TABLE 5
Operating Conditions of the CPD Distillation Column

| | |
| --- | --- |
| Overhead pressure | 0.5 Kg/cm$^2$ · G |
| Overhead temperature | 50° C. |
| Bottom temperature | 175° C. |

TABLE 7
Operating Conditions of the MCPD Column

| | |
| --- | --- |
| Overhead pressure | 0.5 Kg/cm$^2$ · G |
| Overhead temperature | 82° C. |
| Bottom temperature | 195° C. |

MCPD with a purity of 94.4 wt % was obtained from the overhead at the rate of 21 g/hr and was recovered as a product. And a fraction containing MCPD dimer, xylene, C$_9$+, etc. was obtained from the bottom at a rate of 139 g/hr.

The composition of the bottom stream of the MCPD column is shown in Table 8.

TABLE 8
Composition of the MCPD Column Bottom Stream

| Component | wt % |
| --- | --- |
| MCPD dimer | 2.6 |
| Xylenes | 64.9 |
| C$_9$+ | 31.4 |
| Others | 1.1 |

The material balances (g/hr) at various parts of the present example are shown in Table 9.

TABLE 9

| Line No. | 8 | 18 | 10 | 11 | 13 | 14 | 16 | 17 |
| --- | --- | --- | --- | --- | --- | --- | --- | --- |
| CPD | | | 168.96 | | 168.55 | 0.16 | 0.41 | |
| CPD dimer | 204.00 | 204.00 | | 35.04 | | | | |
| MCPD | | | 26.40 | | 1.45 | 12.0 | 19.82 | |
| MCPD dimer | 36.00* | 39.61* | | 13.21* | | 12.64 | | 3.61 |
| CPD · MCPD codimer | | | | | | { 0.25 ⎰ 0.31 | | |
| Interpolymer of MCPD with others | | 1.52 | | 1.52 | | | | 1.52 |
| Xylenes | 420.00 | 510.21 | 90.75 | 419.46 | | 90.75 | 0.54 | 90.21 |
| C$_9$+ and others** | 5340.00 | 5383.66 | 43.89 | 5339.77 | | 43.89 | 0.23 | 43.66 |
| Total | 6000.00 | 6139.00 | 330.00 | 5809.00 | 170.00 | 160.00 | 21.00 | 139.00 |

*including codimer
**isoprene, 1,3-pentadiene, dimers thereof, etc.

CPD with a purity of 99.1% was withdrawn from the CPD column overhead at a rate of 170 g/hr and was recovered as a product. And MCPD dimer, C$_9$+, and xylene fractions were withdrawn from the bottom at a rate of 160 g/hr. The composition of the bottom stream of CPD column is shown in Table 6.

TABLE 6
Composition of the CPD Column Bottom Stream

| Component | wt % |
| --- | --- |
| CPD | 0.1 |
| MCPD | 7.5 |
| MCPD dimer | 7.9 |
| Xylenes | 56.7 |
| C$_9$+ | 27.4 |
| Others | 0.4 |

The bottom stream with the composition shown in Table 6 were charged to the bottom part of an MCPD distillation column (an Oldershow distillation column with 7 plates, with the size of 38 mm diameter, 400 mm height, and equipped with a heater at the bottom).

The operating conditions of the MCPD distillation column are shown in Table 7.

We claim:

1. A process for recovering cyclopentadiene from a cracked gasoline fraction which comprises:

feeding a cracked gasoline fraction which is formed as a by-product in the thermal or steam cracking of a liquid hydrocarbon to a benzene-toluene-xylene distillation column which provides benzene, toluene, and xylene as the overhead stream;

withdrawing the internal reflux stream from the stripping section of said distillation column and feeding said withdrawn internal reflux stream to a depolymerization-distillation column in which said stream is depolymerized by heating at 160°–230° C. for 10–200 minutes;

withdrawing the bottom stream from the depolymerization-distillation column and feeding it into said benzene-toluene-xylene distillation column at a position which is situated below the position from which said internal reflux stream is withdrawn;

withdrawing an overhead stream from said depolymerization-distillation column and feeding it to a cyclopentadiene distillation column which is operated at a bottom temperature of 160°–230° C. with a residence time of 0.25–6 hours, and at an overhead pressure of 0–2 Kg/cm$^2$·G, and at an overhead temperature of 35°–80° C. wherein said cyclopentadiene is distilled as the overhead; and withdrawing said distilled cyclopentadiene from the overhead of said cyclopentadiene column.

2. The process of claim 1, wherein in said depolymerization-distillation column the overhead pressure is 0–5 Kg/cm$^2$·G and the overhead temperature is 140°–210° C.

3. The process of claim 2, wherein the bottom stream from said cyclopentadiene column is withdrawn and fed to said depolymerization-distillation column.

4. A process for recovering cyclopentadiene and methylcyclopentadiene from a cracked gasoline fraction which comprises:

feeding a cracked gasoline fraction which is formed as a by-product in the thermal or steam cracking of a liquid hydrocarbon to a benzene-toluene-xylene distillation column which provides benzene, toluene, and xylene as the overhead stream;

withdrawing the internal reflux stream from stripping section of said distillation column and feeding said withdrawn internal reflux stream to a depolymerization-distillation column in which said stream is depolymerized by heating at 170°–230° C. for 10–200 minutes;

withdrawing the bottom stream from the depolymerization-distillation column and feeding it into said benzene-toluene-xylene distillation column at a position which is situated below the position from which said internal reflux stream is withdrawn;

withdrawing an overhead stream from said depolymerization-distillation column and feeding it to a cyclopentadiene distillation column which is operated at a bottom temperature of 160°–230° C. with a residence time of 0.25–6 hours, and at an overhead pressure of 0–2 Kg/cm$^2$·G, and at an overhead temperature of 35°–80° C. wherein said cyclopentadiene is distilled as the overhead; and withdrawing said distilled cyclopentadiene from the overhead of said cyclopentadiene column;

withdrawing the bottom stream from the cyclopentadiene distillation column and feeding it to a methylcyclopentadiene distillation column which is operated at a bottom temperature of 170°–210° C. with a residence time of 0.5–5 hours, and at an overhead pressure of 0–2 Kg/cm$^2$·G and at an overhead temperature of 65°–115° C. wherein methylcyclopentadiene is distilled as the overhead; and withdrawing said distilled methylcyclopentadiene from the overhead of said methylcyclopentadiene distillation column.

5. The process of claim 4, wherein in said depolymerization-distillation column the overhead pressure is 0–5 Kg/cm$^2$·G and the overhead temperature is 140°–210° C.

6. The process of claim 5, wherein the bottom stream from said methylcyclopentadiene column is withdrawn and fed to said depolymerization-distillation column.

* * * * *